(12) United States Patent
Van Grinsven et al.

(10) Patent No.: US 9,228,970 B2
(45) Date of Patent: Jan. 5, 2016

(54) HEAT-TRANSFER RESISTANCE BASED ANALYSIS BIOPARTICLES

(75) Inventors: Bart Van Grinsven, Heerlen (NL); Ward De Ceuninck, Nerem (BE); Patrick Wagner, Vilvoorde (BE); Luc Michiels, Mol (BE)

(73) Assignees: IMEC, Leuven (BE); Universiteit Hasselt, Diepenbeek (BE)

( * ) Notice: Subject to any disclaimer, the term of this patent is extended or adjusted under 35 U.S.C. 154(b) by 46 days.

(21) Appl. No.: 13/991,227

(22) PCT Filed: Nov. 25, 2011

(86) PCT No.: PCT/EP2011/071089
§ 371 (c)(1),
(2), (4) Date: Jun. 3, 2013

(87) PCT Pub. No.: WO2012/076349
PCT Pub. Date: Jun. 14, 2012

(65) Prior Publication Data
US 2014/0011198 A1    Jan. 9, 2014

Related U.S. Application Data

(60) Provisional application No. 61/421,143, filed on Dec. 8, 2010.

(51) Int. Cl.
C12M 1/34 (2006.01)
C12M 3/00 (2006.01)
(Continued)

(52) U.S. Cl.
CPC .......... *G01N 27/327* (2013.01); *B01L 3/50273* (2013.01); *B01L 3/502738* (2013.01);
(Continued)

(58) Field of Classification Search
USPC ........... 435/6.1, 6.11, 283.1, 287.2; 422/68.1, 422/82.02, 82.12, 430; 536/23.1, 24.3
See application file for complete search history.

(56) References Cited

U.S. PATENT DOCUMENTS

2003/0059807 A1*  3/2003  Roach et al. ...................... 435/6
2006/0078999 A1*  4/2006  Bell et al. ...................... 436/147

FOREIGN PATENT DOCUMENTS

WO        2004/079001 A1    9/2004

OTHER PUBLICATIONS van Grinsven et al, Heat-Transfer Resistance at Solid Liquid Interfaces: A Tool for the Detection of Single-Nucleotide Polymorphisms in DNA, 2012, ACS NANO, 6, 2712-2721.*
(Continued)

*Primary Examiner* — Narayan Bhat
(74) *Attorney, Agent, or Firm* — McDonnell Boehnen Hulbert & Berghoff LLP (57) ABSTRACT

A method an system is disclosed for characterizing DNA and/or RNA duplexes. The biosensing device comprises a heating element using a power and being suitable for providing thermal denaturation of target DNA and/or RNA bioparticles, a sample holder adapted for receiving a biocompatible substrate having a functionalized surface which is coated with probe DNA and/or RNA whereto target DNA and/or RNA duplexes can be attached, the sample holder further being adapted for exposing the biocompatible substrate at one side to the heating element, a first temperature sensing element for sensing a temperature at the side where the biocompatible substrate can be exposed to the heating element and a second temperature sensing element for sensing a temperature at the side opposite thereto with respect to the biocompatible substrate. The device also comprises a processing means programmed for calculating at least one heat transfer resistivity value based on temperature values obtained with the first temperature sensing element and the second temperature sensing element and the power for the heating element, for deriving a characteristic of the target DNA and/or RNA bioparticles from said heat transfer resistivity value.

20 Claims, 4 Drawing Sheets

(51) Int. Cl.
| | |
|---|---|
| *C12M 1/00* | (2006.01) |
| *C12Q 1/68* | (2006.01) |
| *C07H 21/02* | (2006.01) |
| *C07H 21/04* | (2006.01) |
| *G01N 15/06* | (2006.01) |
| *G01N 27/00* | (2006.01) |
| *G01N 25/00* | (2006.01) |
| *G01N 31/22* | (2006.01) |
| *G01N 27/327* | (2006.01) |
| *G01N 27/02* | (2006.01) |
| *B01L 3/00* | (2006.01) |
| *G05B 15/02* | (2006.01) |

(52) U.S. Cl.
CPC ............ *C12Q1/6825* (2013.01); *C12Q 1/6827* (2013.01); *C12Q 1/6832* (2013.01); *G01N 27/021* (2013.01); *G01N 27/3275* (2013.01); *G05B 15/02* (2013.01); *B01L 2300/023* (2013.01); *B01L 2300/0636* (2013.01); *Y10T 436/11* (2015.01); *Y10T 436/143333* (2015.01)

(56) References Cited

OTHER PUBLICATIONS

PCT International Search Report, PCT International Application No. PCT/EP2011/071089 dated Apr. 25, 2012.

Van Grinsven, Bart et al., "Heat-Transfer Resistance at Solid-Liquid Interfaces: A Tool for the Detection of Single-Nucleotide Polymorphisms in DNA", ACS Nano, vol. 6, No. 3, Mar. 27, 2012, pp. 2712-2721.

Velizhanin, Kirill A. et al., "Driving Denaturation: Nanoscale Thermal Transport as a Probe of DNA Melting", Physical Review, vol. 83, No. 5, May 1, 2011, pp. 1-7.

Vermeeren, V. et al., "Topographical and Functional Characterization of the ssDNA Probe Layer Generated Through EDC-Mediated Covalent Attachment to Nanocrystalline Diamond Using Fluorescence Microscopy", Langmuir, vol. 24, No. 16, Jul. 16, 2008, pp. 9125-9134.

Wenmackers, Sylvia et al., "Diamond-Based DNA Sensors: Surface Functionalization and Read-Out Strategies", Phys. Status Solidi, No. 3, Jan. 26, 2009, pp. 391-408.

\* cited by examiner

HEAT-TRANSFER RESISTANCE BASED ANALYSIS BIOPARTICLES

CROSS-REFERENCE TO RELATED APPLICATIONS

This application is a U.S. National Phase Application of International Patent Application No. PCT/EP2011/071089 filed on Nov. 25, 2011, which claims the benefit of priority of U.S. Provisional Patent Application Ser. No. 61/421,143, filed Dec. 8, 2010.

FIELD OF THE INVENTION

The present disclosure is related to detection and/or characterisation of particles such as bioparticles. More particular, the present invention relates to a method and system for detecting or characterizing particles such as DNA and/or RNA particles.

BACKGROUND OF THE INVENTION

The detection and identification of single-nucleotide polymorphisms (SNPs) in DNA is of central importance in genomic research for two different reasons. First, SNPs are responsible for, or at least involved in, several hundreds of inherited diseases such as Alzheimer, mucoviscidosis, phenylketonuria, and several types of breast- and colon cancer. Second, SNPs involved in the regulation of the liver function have an impact on the metabolism of drugs, which is related to the rapidly emerging field of theranostics or 'personalized medicine'. SNPs can be characterized by hybridization-based assays such as microarrays: the massive parallelized readout is an advantage, but the method requires fluorescent labelling, optical readout, elevated reaction temperatures (~80° C.) and elongated hybridization times of ~16 hours. Even under these circumstances, thermal equilibrium between probe- and target DNA is not always guaranteed and the method has an 'end-point' character rather than providing dynamic information on molecular recognition between complementary or mismatched fragments. Finally, only defects can be detected for which a correspondingly defective probe-DNA strand was included in the microarray in order to establish nevertheless stable duplexes. Due to these drawbacks, unknown mutations are frequently identified by denaturation based approaches. Widespread methods are real-time PCR (polymerase chain reaction) with associated melting-curve analysis and denaturing gradient gel electrophoresis DGGE. DGGE operates either with a pH-gradient or a temperature gradient along the electrophoretic path/lanes and is based on the fact that DNA duplexes with SNP defects have a lowered stability with respect to chemical or thermal denaturation. As drawbacks, real-time PCR requires fluorescent labelling and expensive instrumentation while DGGE is time consuming, severely limited towards parallelized analyses, and is an endpoint analysis without information on the kinetics of the denaturation process. To overcome these current limitations, several label-free electronic, 'real-time' techniques have been proposed in literature. For its analogy with chemical DGGE, we mention the impedimetric denaturation monitoring upon exposure to NaOH reported by van Grinsven et al. in the international patent application entitled "A biosensor using impedimetric real-time monitoring" and co-pending herewith. This gave clear evidence that the presence or absence of SNPs can be derived from the denaturation-time constant within a time scale of 1 to 2 minutes.

Despite of all recent progress, there still is room for an accurate denaturation based detection technique for characterising or analysing DNA/RNA based bioparticles.

SUMMARY OF THE INVENTION

It is an object of embodiments of the present invention to provide a good method and a sensing device for the detection and/or characterization of DNA and/or RNA based biomolecules which is label-free and reliable.

It has surprisingly been found that there is a substantially higher heat-transfer resistance between a sensor surface covered with a single-stranded molecular DNA and/or RNA brush and the surrounding electrolyte compared to the low heat-transfer resistance of the double stranded DNA and/or RNA brush and the surrounding electrolyte below the melting transition. Embodiments of the present invention make advantage of this physical phenomenon for characterising and/or detecting DNA and/or RNA based molecules.

It is an advantage of embodiments according to the present invention that the change in heat-transfer resistance is significantly high, thus allowing sensitive detection. It is an advantage of embodiments of the present invention that the change in heat-transfer resistance can be larger than 5%, e.g. 10% or larger, e.g. between 10% and 20%, in contrast to e.g. calorimetric effects emerging from the binding or unbinding energies during denaturation of double stranded DNA and/or RNA.

It is an advantage of embodiments according to the present invention that analysis or characterisation can be based on thermally induced on-chip denaturation.

It is an advantage of embodiments of the present invention that the detection and/or characterization can be obtained in a cheap way, i.e. without requiring an expensive setup, basically requiring only an adjustable heat source and at least two thermometers.

It is an advantage of embodiments according to the present invention that methods and systems for characterisation and/or detection of DNA and/or RNA based bioparticles can be performed in real-time.

It is an advantage of embodiments of the present invention that a method and sensing device for the detection and/or allocation of point mutations in DNA and/or RNA based biomolecules can be provided, whereby the sensor used for the detection and characterization is suitable for multiple-term measurements and can be used repetitively, i.e. is re-usable.

It is an advantage of embodiments according to the present invention that a biosensor based on a novel detection principle is obtained, different from electronic impedance spectroscopy, electric field effects, surface-band bending, mass loading, and fluorescence quenching.

It is an advantage of embodiments of the present invention that a sensing device can be obtained that works as a cartridge and a reader, so that only the cartridge needs to be replace, resulting in an economically interesting device.

The above object is accomplished by a method and device according to the present invention.

The present invention relates to a bio-sensing device suitable for the detection and/or characterization of target DNA and/or RNA bioparticles, the bio-sensing device comprising a heating element for heating using a power, the heating element being suitable for providing thermal denaturation of target DNA and/or RNA bioparticles, a sample holder adapted for receiving a biocompatible substrate having a functionalized surface which is coated with probe DNA and/or or RNA whereto target DNA and/or RNA duplexes can be attached, the sample holder further being adapted for exposing the biocompatible substrate at one side to the heating element, a first temperature sensing element for sensing a temperature at the side where the biocompatible substrate can be exposed to the heating element and a second temperature sensing element for sensing a temperature at the side opposite thereto with respect to the biocompatible substrate, and a processing means programmed for calculating at least one heat transfer resistivity value based on temperature values obtained with the first temperature sensing element and the second temperature sensing element and the power for the heating element, for deriving a characteristic of the target DNA and/or RNA bioparticles from said heat transfer resistivity value. It is an advantage of embodiments according to the present invention that a system is provided allowing to determine DNA/RNA characteristics based on measurements of the heat transfer resistivity.

The processing means may be adapted for determining a heat transfer resistivity as function of temperature. The temperature referred to may be the temperature sensed with the first temperature sensing element.

The processing means may be adapted for determining at least two heat transfer resistivity values as function of temperature, one at a temperature sensed with the first temperature sensing element below the expected thermal denaturation temperature as sensed with the first temperature sensing element and one at a temperature above the expected thermal denaturation temperature as sensed with the first temperature sensing element. It is an advantage of embodiments according to the present invention that characterisation of the DNA and/or RNA bioparticles can already be done based on thermal measurements at two different temperatures.

The biosensing device may comprise, at a side of the biocompatible substrate opposite to the thermal element, a fluidic compartment for exposing that side of the biocompatible substrate to a fluid, the second temperature sensing element being positioned in the fluid compartment. It is an advantage of embodiments according to the present invention that appropriate measurement conditions can be easily generated by using an appropriate fluid at the side of the biocompatible substrate. The fluid may be used for introducing the target DNA and/or RNA. The device may comprise a flow cell comprising the fluid compartment and furthermore comprising a pumping and/or valve system for transferring fluid from and to the fluid compartment.

The processing means may be adapted for determining, based on the at least one heat transfer resistivity, a characteristic of the target DNA and/or RNA duplexes. It is an advantage of embodiments according to the present invention that use can be made of a new detection technique based on thermal measurements for determining characteristics of DNA and/or RNA bioparticles.

The characteristic of the target DNA and/or RNA duplexes may be at least one point mutation therein.

The heating element may be controlled by a power resistor operating providing an input power. It is an advantage of embodiments according to the present invention that use can be made of known heating elements and heating technology, such elements being readily available and easy to manufacture, install and/or calibrate.

The first temperature sensing element and/or the second temperature sensing element may be a thermocouple. It is an advantage of embodiments according to the present invention that use can be made of known temperature sensing elements, which are readily available and easy to manufacture, install and/or calibrate.

The biosensing device may comprise a controller for controlling the heat element and for controlling the temperature sensing elements for obtaining input power and temperature values for different temperatures as sensed with the first temperature sensing element.

The present invention also relates to a method for characterising a target DNA and/or RNA bioparticle, e.g. DNA and/or RNA duplexes, the method comprising obtaining a biocompatible substrate comprising a functionalized surface which is coated with probe DNA and/or RNA whereto the target DNA and/or RNA bioparticles are attached, providing a heating power using a power at a first side of the biocompatible substrate, sensing at least a temperature at the first side of the biocompatible substrate and at a second side, opposite to the first side with respect to the biocompatible substrate, and calculating at least one heat transfer resistivity value based on the temperature values obtained at the first side and the second side and the power for deriving a characteristic of the target DNA and/or RNA from said heat transfer resistivity value.

The method may comprise deriving a characteristic of the target DNA and/or RNA from said heat transfer resistivity value.

Calculating may comprise determining a heat transfer resistivity as function of temperature.

Determining a heat transfer resistivity as function of temperature may comprise determining at least two heat transfer resistivity values as function of temperature, one at a temperature sensed with the first temperature sensing element below the expected thermal denaturation temperature as sensed with the first temperature sensing element and one at a temperature above the expected thermal denaturation temperature as sensed with the first temperature sensing element.

The method may comprise providing a fluid in contact with the functionalized surface which is coated with probe DNA and/or RNA.

Obtaining a biocompatible substrate may comprise attaching the target DNA and/or RNA bioparticles, e.g. DNA and/or RNA duplexes, to a functionalized surface which is coated with probe DNA and/or RNA.

The substrate may be nanocrystalline diamond (NCD).

The substrate may be a semiconductor substrate having a diamond coating with a thickness between 50 nm and 150 nm on at least one of its surface.

The functionalized surface may comprise a first layer of fatty acid(s) such as 10-undecenoic fatty acid.

The functionalized surface may comprise a second layer provided onto said first layer and containing the probe DNA and/or RNA.

The probe DNA and/or RNA may be NH2-modified single stranded DNA (ssDNA). Attaching the target DNA and/or RNA bioparticles, e.g. DNA and/or RNA duplexes, to the functionalized surface may be performed by hybridization of the target DNA duplexes with the probe ssDNA molecules.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

BRIEF DESCRIPTION OF THE DRAWINGS

TABLE 1 illustrates base sequences of the probe DNA and target DNA employed in hybridisation and denaturation experiments for illustrating features and advantages of embodiments according to the present invention.

TABLE 2 illustrates experimentally obtained data of thermally-induced denaturation measured with heat-transfer characterisation in comparison with time constants of isiothermal, chemically induced denaturation, illustrating features and advantages of embodiments according to the present invention.

All figures are intended to illustrate some aspects and preferred embodiments. The figures are depicted in a simplified way for reason of clarity. Not all alternatives and options are shown and the invention is not limited to the content of the given drawings.

DEFINITIONS

The term "DNA denaturation" as referred to in the claims and the description is used to define the process by which double-stranded DNA unwinds and separates into single-stranded DNA through the breaking of hydrogen bonding between the bases. Throughout the description said denaturation process refers to the separation of DNA strands. A similar definition can be applied for RNA denaturation with reference to unwinding of double-stranded RNA and separation into single-stranded RNA through the breaking of hydrogen bonding between the bases. In embodiments of the present invention, denaturation may be induced thermally.

The term "DNA Hybridization" as referred to in the claims and/or the description is used to define the process of establishing a non-covalent, sequence-specific interaction between two or more complementary strands of nucleic acids into a single hybrid, which in the case of two strands is referred to as a duplex. Oligo-nucleotides, DNA, or RNA will bind to their complement under normal conditions, so two perfectly complementary strands will bind to each other readily.

The term "single-nucleotide polymorphism" refers to a DNA sequence variation occurring when a single nucleotide—A, T, C, or G—in the genome differs between members of a species or paired chromosomes in an individual.

The term "denaturation time constant" refers to the time needed to unfold the double helix structure of the DNA sequences, in the sense that the covalently attached probe-DNA sequence stays on the diamond surface.

Although in embodiments according to the present invention and examples thereof described in the present description, illustration typically is performed for and reference typically is made to DNA, embodiments and examples are not limited thereto and can, mutates mutandis be applied to RNA.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Moreover, the term top and the like in the description and the claims are used for descriptive purposes and not necessarily for describing relative positions. It is to be understood that the terms so used are interchangeable under appropriate circumstances and that the preferred embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary preferred embodiments, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination. In the description provided herein, numerous specific details are set forth. However, it is understood that preferred embodiments may be practiced without these specific details. In other instances, well-known methods, structures and techniques have not been shown in detail in order not to obscure an understanding of this description.

The invention will now be described by a detailed description of several preferred embodiments. It is clear that other preferred embodiments can be configured according to the knowledge of persons skilled in the art without departing from the true spirit or technical teaching of the invention as defined by the appended claims. All references cited herein are incorporated herein by reference in their entirety. To the extent publications and patents or patent applications incorporated by reference contradict the disclosure contained in the specification, the specification is intended to supersede and/or take precedence over any such contradictory material.

It was surprisingly found that the denaturation of double stranded DNA and/or RNA bioparticles can be detected in the heat transfer resistivity and that this can be used for characterising DNA and/or RNA.

Where in embodiments according to the present invention reference is made to heat transfer resistivity $R_{th}$, reference is made to the ratio of the temperature difference $\Delta T$ of the temperature at each side of the substrate comprising the target DNA and/or RNA bioparticles to the input power P, i.e. $R_{th}=\Delta T/P$.

Figure 1:
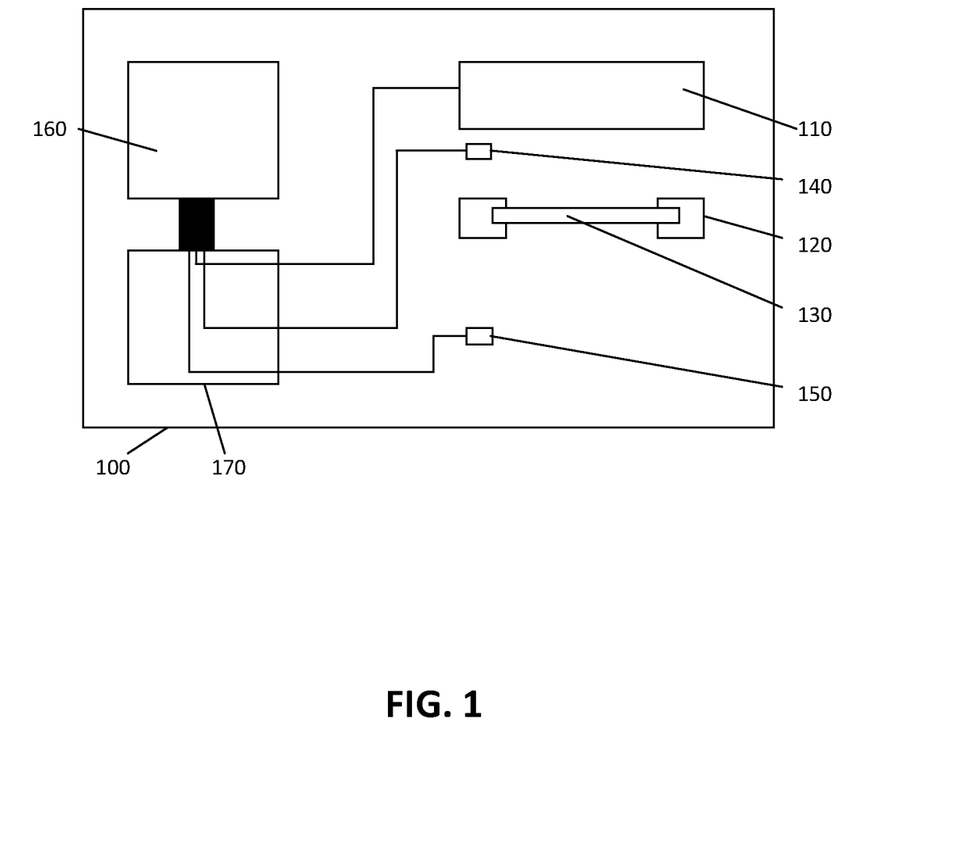
FIG. 1 illustrates a schematic view of a system according to an embodiment of the present invention.

According to a first aspect, a bio-sensing device 100 is disclosed for characterising DNA and/or RNA bioparticles. The biosensing device 100 may be adapted for detecting and identifying single-nucleotide polymorphisms (SNPs) in DNA and/or RNA duplexes. The latter can be performed in an efficient and label-free manner. Use of the biosensor does not only make it possible to detect the presence of point mutations (single-nucleotide polymorphisms) but also the location of said point mutation in the target DNA and/or RNA. Moreover, this can be performed in an accurate manner according to embodiments of the present invention. According to embodiments of the present invention, the bio-sensing device 100 comprises a heating element 110 suitable for providing thermal denaturation of target DNA and/or RNA bioparticles. By way of illustration, embodiments of the present invention not limited thereto, a schematic overview of standard and optional components is shown in FIG. 1.

Such a heating element 110 may in one example be a block of solid material and a heating element, e.g. a power resistor providing an input power. In principle any type of heating element may be used. The heating element according to embodiments typically is adapted—e.g. in relative position with respect to the sample or sample-substrate—so that a temperature gradient is created over the sample or sample-substrate. Heating elements thus may be used that provide a heating source at one side of the sample or sample-substrate, which transfers through the sample, and then goes into the fluid positioned at the opposite side of the sample or sample-substrate (i.e. opposite to the heating element, with reference to the substrate. The biosensor 100 furthermore may comprise a sample holder 120 adapted for receiving a biocompatible substrate 130 having a functionalized surface which is coated with probe DNA and/or RNA whereto target DNA and/or RNA duplexes can be attached. The sample holder furthermore is adapted for exposing the biocompatible substrate at one side to the heating element. The device 100 furthermore comprises a first temperature sensing element 140 for sensing a temperature at the side where the biocompatible substrate can be exposed to the heating element and a second temperature sensing element 150 for sensing a temperature at the side opposite thereto with respect to the biocompatible substrate 100. Such temperature sensing elements 140, 150 can be any type of temperature sensing elements 140, 150, one example being a thermocouple. The device 100 also may comprise more than two sensing elements, such as for example an array of temperature sensing elements, although for operating embodiments of the invention, two temperature sensing elements are sufficient. The biosensing device 100 furthermore comprises a processing means 160 programmed for calculating at least one heat transfer resistivity value based on temperature values obtained with the first temperature sensing element and the second temperature sensing element and an input power for the heating element. According to embodiments of the present invention, the processing means 160 is programmed for using the calculated values for deriving a characteristic of the target DNA and/or RNA bioparticles from said heat transfer resistivity value. In advantageous embodiments, the processor or processing means 160 is adapted for determining a heat transfer resistivity as function of temperature. In one embodiment, this may be determining at least two heat transfer resistivity values as function of temperature, one at a temperature sensed with the first temperature sensing element below the expected thermal denaturation temperature as sensed with the first temperature sensing element and one at a temperature above the expected thermal denaturation temperature as sensed with the first temperature sensing element. The processing means 160 furthermore may be adapted for filtering the data, to improve signal to noise ratio. The processing means 160 furthermore may be adapted for deriving from the heat transfer resistivity values a characteristic of the DNA and/or RNA bioparticles. Such a characteristics may for example be the presence of a point defect. The latter can be based on comparison with previously performed measurements. The processing means 160 may be adapted for taking into account experimental conditions, such as for example taking into account a heating rate or taking into account a position of the DNA and/or RNA bioparticles with respect to the heating element (i.e. the bioparticles being at the side of the heating element with respect to the remaining part of the biocompatible substrate or at the opposite side thereof). The processing means 160 may be programmed for performing the above in an automated way. Such processing means 160 may be a software based processor, as well as a hardware based processor. It may for example make use of a predetermined algorithm, a look up table or a neural network for performing the processing. According to some embodiments of the present invention, the biosensing device 100 may comprise a fluidic compartment for exposing the second side of the biocompatible substrate to a fluid. The second temperature sensing element being positioned in the fluid compartment. The fluid may be used for introducing the target DNA and/or RNA. The biosensing device 100 may comprise a flow cell comprising the fluid compartment and furthermore comprising a pumping and/or valve system for transferring fluid from and to the fluid compartment. According to some particular embodiments, the flow cell may comprise a syringe system coupled to a Perspex flow cell with a suitable inner volume. The dimensions of said inner volume are optimised towards the final device goals. To set up a test device an example was shown having a suitable inner volume of around 110 µl. The effective area of the functionalized substrate surface depends on the dimensions of the flow cell and may be in the order of around 28 mm2 exposed to the liquid. In some embodiments, the electrode may be sealed with an O-ring. The operation of the biosensing device may be controlled by a controller 170. A controller 170 may control the heat element and the temperature sensing elements for obtaining input power and temperature values. Such values may be obtained for different input powers, or—corresponding therewith—for different temperatures as sensed with the first temperature sensing element.

The system also may be equipped with electrodes for measuring an impedance or with a transparent bottom for measuring a fluorescence signal, as the measurement principle can be easily combined with other measurement techniques, e.g. for cross-checking. Further optional features and advantages may be as described in the example below.

In a second aspect, the present invention also relates to a method for characterising a target DNA or RNA bioparticle, e.g. a target DNA and/or RNA duplex. The method may be especially suitable for studying point mutations in DNA and/or RNA bioparticles, although embodiments are not limited thereto. According to embodiments of the present invention, the method comprises obtaining a biocompatible substrate comprising a functionalized surface which is coated with probe DNA and/or RNA whereto the target DNA and/or RNA bioparticles are attached and providing a heating power using a power at a first side of the biocompatible substrate. The latter results in a temperature gradient being present over the biocompatible substrate and thus over the sample to be characterised. The method also comprises sensing at least a temperature at the first side of the biocompatible substrate and at a second side, opposite to the first side with respect to the biocompatible substrate. From these measurements and the power for the heating element used, according to embodiments of the present invention, at least one heat transfer resistivity value is calculated for deriving a characteristic of the target DNA and/or RNA from the heat transfer resistivity value. By way of example, a savitsky golay filter could be used, although embodiments of the present invention are not limited thereto. In some embodiments, calculating at least one heat transfer resistivity value comprises determining the heat transfer resistivity as function of temperature, i.e. determining different heat transfer resistivity values at different temperatures. The calculating may furthermore include applying a filter for improving the signal to noise ratio. The temperature used as reference can in principle be chosen and may for example be the temperature senses with the first temperature sensing element. In one embodiment, determining the heat transfer resistivity as function of temperature comprises determining at least two heat transfer resistivity values as function of temperature, one at a temperature sensed with the first temperature sensing element below the expected thermal denaturation temperature as sensed with the first temperature sensing element and one at a temperature above the expected thermal denaturation temperature as sensed with the first temperature sensing element. In embodiments according to the present invention, the biocompatible substrate, more particularly the functionalized surface thereof which is coated with the probe DNA and/or RNA is brought into contact with a fluid, and temperature sensing on this side occurs in the fluid. Obtaining the biocompatible substrate can be performed in a plurality of manners. The biocompatible substrate may be previously made. In some embodiments obtaining the biocompatible substrate comprises inserting or positioning or fixing the biocompatible substrate on or in the substrate holder. The latter may correspond with inserting of a sample substrate (as a cartridge) into a cartridge reader. In alternative embodiments, the substrate is not fully prepared yet. In some embodiments, obtaining the substrate may imply obtaining a nanocrystalline diamond substrate and/or coating a substrate with a diamond coating, e.g. having a thickness between 50 nm and 150 nm). In some embodiments, the method may include functionalising the surface. Functionalising the surface may be providing a first layer of fatty acid(s) to the surface, e.g. on the diamond coating. Such a fatty acid may be any suitable type of fatty acid, such as for example 10-undecenoic fatty acid. In some embodiments, functionalising the surface also may comprises providing, besides a first layer, a second layer on top of the first layer, whereby the second layer comprises the probe DNA and/or RNA. In other embodiments, a biocompatible substrate comprising already the probe DNA and/or RNA is obtained. In one embodiment, the probe DNA may be NH2 modified single stranded DNA. In some embodiments obtaining a biocompatible substrate also may comprise attaching the target DNA and/or RNA bioparticles to a functionalised surface coated with probe DNA and/or RNA. Such attaching may be performed in one embodiment by attaching target DNA duplexes to probe single stranded DNA molecules by performing hybridisation. Further optional steps of the method according to embodiments of the present invention may be express the functionality of components described in the first aspect, or may correspond with features as described in the example below.

In a third aspect, the present invention also relates to a controller adapted for controlling a heating element, temperature sensing elements and a processor for performing a method according to embodiments of the second aspect of the present invention. Such a controller may be part of a system as described in the first aspect or may be suitable for communicating therewith. The controller may be implemented as software—to be implemented on a processor—or may be implemented as hardware. The controller may be implemented, such that after activation and obtaining the biocompatible substrate, the sensing, calculating and where included the deriving step occurs in an automated and/or automatic way. The controller may be programmed, e.g. it may include a microprocessor or an FPGA whereon a set of instructions are implemented. Alternatively, the controller can be software based and thus may correspond with a computer program product. The present invention also relates to a computer program product providing, when run on a computer, the functionality of any of the methods as described in the second aspect. Such a computer program product may be carried on a data carrier, the invention thus also relating to a data carrier, such as a CD-ROM, a disk, a USB memory device, a DVD, a pc, a work station, . . . storing the computer program product in a machine readable form or to the transmission of such a computer program product over a network, e.g. local or wide area network.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

By way of illustration, embodiments of the present invention not being limited thereto, examples are provided of a particular biosensor and of experimental results obtained therewith, illustrating features and advantages of embodiments according to the present invention.

Figure 2:
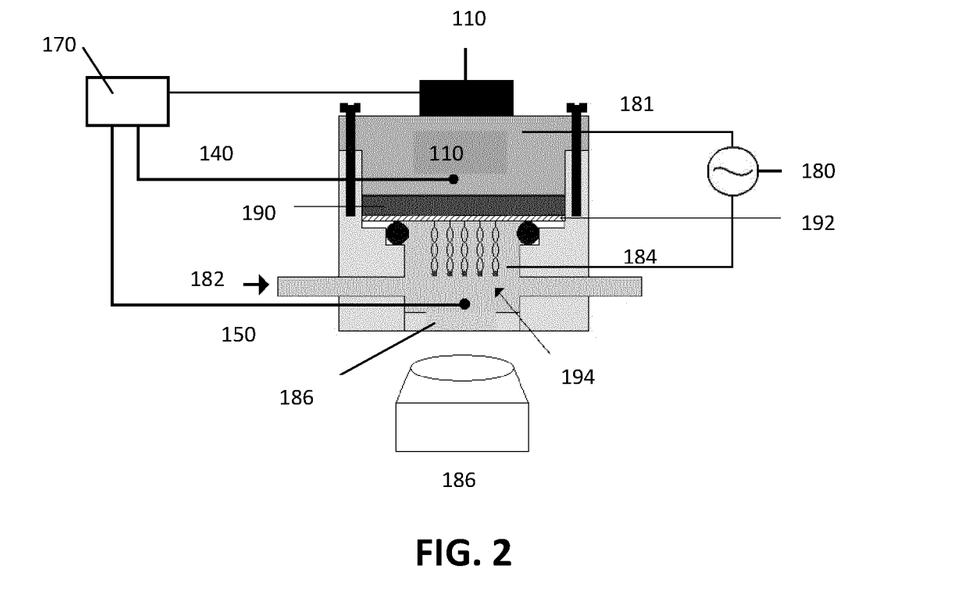
FIG. 2 illustrates a more detailed schematic view of an exemplary setup for measuring a change in heat-transfer capacity according to an embodiment of the present invention.

Experiments were performed based on a biosensor as illustrated in FIG. 2. In the exemplary embodiment, the hart piece is a silicon chip (10 by 10 mm$^2$) 190 covered with a thin layer of boron-doped, nanocrystalline diamond (NCD) 192. The specific choice for nanocrystalline diamond (NCD) electrodes arises from the fact that this material is intrinsically biocompatible and it allows for the covalent immobilization of biochemical receptors by various techniques. Examples known from literature are the binding of proteins and DNA fragments, where a manifold of denaturation-rehybridization cycles has been demonstrated without loss of binding capacity. An overview of functionalization strategies, both on oxygen- and on hydrogen terminated diamond surfaces, can be found in the review articles by Wenmackers et al. in Physica Status Solidi (a) 206 pp 391-408 (2009) and Vermeeren et al. in Langmuir 24 pp 9125-9134 (2008). Furthermore, diamond offers a wide electrochemical window and it is chemically and physically stable at elevated temperatures, under extreme pH conditions, and in solutions with high ionic strengths. These elements make NCD a universal electrode material for monitoring biochemical reactions in real time. DNA-hybridization sensors based on diamond as a platform material in combination with impedance spectroscopy, solution-gate FETs, and cyclic voltammetry with a redox mediator on diamond nanowires are known by the person skilled in the art. Here, the planar sensor electrodes were prepared by plasma-enhanced chemical vapour deposition (PE-CVD) from methane/hydrogen mixtures in an ASTEX-type reactor. The substrates were 2-inch silicon wafers (thickness 500-550 μm, crystalline orientation (100), p-type doped with resistivities from 1 to 20 Ωcm), which were diced into samples of 10 mm by 10 mm after deposition. The diamond layers had a typical thickness of 100 nm with an average grain size of 50 nm as determined by x-ray diffraction. Due to the nanocrystalline character of the diamond coating, no preferential crystallographic orientation was detectable. To ensure a good electrical conductivity of the diamond layer (range of 1 Ωcm), the PE-CVD deposition was done with an admixture of trimethyl borane (B(CH$_3$)$_3$) to the CH$_4$ gas with a concentration ratio of 200 ppm B/C.

The diamond layer served as an immobilization platform onto which 29-mers of ds-DNA are covalently bound via the 'fatty acid & EDC' coupling route as known from prior art. The as-prepared diamond electrodes were hydrogenated in H$_2$ plasma (50 Torr, 800° C., power 4000 W, duration of 14 min) to facilitate the attachment of the fatty-acid linker molecules as described in the next paragraph. First, 10-undecenoic fatty acid was photochemically attached to the H-terminated NCD electrodes by UV illumination (wavelength 254 nm, intensity 265 mW/cm$^2$) during 20 hours under a protective N$_2$ atmosphere. The reaction mechanism is presumably based on the fact that the hydrophobic C=C end of the fatty acid is oriented towards the H-terminated diamond surface and mediated by photoemission from the surface as proposed in literature for the photochemical grafting of alkenes to silicon surfaces. After this photochemical treatment, the samples were thoroughly rinsed in acidic acid at 100° C. to remove unbound fatty-acid fragments.

The probe ss-DNA was linked to the diamond surface via stable C—C bonds in 'head-on' configuration while the target ss-DNA is free to hybridize or to denature according to experimental conditions without steric hindering.

The sequence of the probe DNA is given in TABLE 1 together with the sequence of four different types of target DNA: the complement, a random sequence, and two sequences hybridizing under formation of a CC mismatch at either base-pair 7 or at base pair 20. Note that for both 1-base mismatch sequences the mismatch is a 'CC' while the nearest neighbours are 'GC' and 'AT' in both cases. The probe DNA exhibits a spacer consisting of 7 A bases while the target DNA fragments carry a fluorescent Alexa 488 label at the 5' end. The spacer was used to avoid border effects at the proximity of the electrode surface. The total amount of probe ssDNA used to functionalize 1 cm$^2$ of electrode surface was 300 pmol. This is in excess of the binding capacity of the surface, but it ensures a rapid functionalization due to the high concentration of available probe DNA. The hybridization conditions were chosen in a way that also defective duplexes with a single-nucleotide mismatch hybridize in a way that they are stable under room-temperature conditions. The hybridisation was performed by incubating ssDNA-modified NCD samples for 2 hours at 30° C. with 600 pmol of Alexa 488-labelled target ssDNA (29 bp) in 10×PCR buffer. During hybridization, the samples were placed in a closed container under a saturated water vapour atmosphere to avoid evaporation of the reaction fluid. After hybridization, the samples were rinsed in 2×SSC buffer containing 0.5% SDS for 30 min at room temperature, followed by two 5 min rinsing steps in 0.2×SSC buffer, once at 5 degrees below the hybridization temperature and once at room temperature.

The measurements were performed in a measurement setup as indicated in FIG. 2. For obtaining the experimental results discussed below, the setup consisted of a homemade impedance spectroscopy unit 180 using coax connectors 181 for connecting to the different elements, a flow pump system being a syringe system 182 and a temperature control unit 170 coupled to a Perspex flow cell with an inner volume of 110 μl. The DNA chip was based on a silicon substrate 190, coated with a diamond coating 192 and comprising DNA target bioparticles 194 to be characterized. The DNA chip (also acting as working electrode) was sealed with an O-ring, resulting in an effective area of 28 mm$^2$ exposed to the liquid. The counter electrode 184 was a gold wire (diameter 500 μm, oriented perpendicular with the flow direction) at a distance of 1.7 mm from the surface of the working electrode. The working electrode was pressed on a copper lid, serving both as heat transducer 110 and back electrode. Miniaturized thermocouples 140, 150 (type K, diameter 500 μm as obtainable from TC Direct, The Netherlands) were integrated in the copper lid (T$_1$) and in the liquid (T$_2$), also 1.7 mm from the surface of the working electrode. For stability purposes the counter electrode was mounted from one end of the flow chamber to the other, resulting in a contact area of 17 mm$^2$. The T2 thermocouple was only sensitive at the tip end and was therefore mounted halfway the flow chamber, thus reaching the center of the chamber, resulting in a contact area of 8.5 mm$^2$. The thermocouple signal (T$_1$) was led to a data acquisition unit (Picolog TC08, Picotech, United Kingdom) and from there processed into a proportional-integral-derivative controller (P=10, D=5, I=0.1). The correct output voltage was calculated and sent out by the controller (NI USB 9263, National Instruments, USA) and sent out to an amplifier. The output voltage was then amplified by a power operational amplifier (LM675, Farnell, Belgium) to provide the necessary power. From here, the output voltage was led to a power resistor (22Ω, MPH 20, Farnell, Belgium) acting as the heating element directly joint to the copper made heat transducer. Furthermore, the cell ws equipped with a quartz-glass bottom, enabling simultaneous fluorescence imaging with an inverted confocal fluorescence microscope 186. The thermocouple T2 was 3.2 mm away from the quartz glass bottom while the thermocouple was placed 2.4 mm away from the quartz-glass 188. The flow cell was connected to a syringe system. The syringe system 182 comprised two identical programmable syringe pumps (ProSense, model NE-500, The Netherlands) enabling flow rates of 0.73 µl/hour to 1699 ml/hour. The impedance spectroscopy unit measured the impedance at a frequency of 1 kHz, ensuring an optimal signal-to-noise ratio (33). The amplitude of the ac voltage was fixed to 10 mV. Temperatures were measured at a sampling rate of 1 sample/second. All measurements were performed at an ambient temperature of 19.3° C. Before measuring, the entire system was checked for bias voltages by measuring the voltage between the gold wire and the diamond electrode but no bias voltage was observed. The denaturation of DNA was monitored as a cross-check by measuring the change in fluorescence intensity, resulting from the ALEXA labels at the 5' terminus of the target-DNA strands, with a Zeiss LSM 510 META Axiovert 200 M laser scanning confocal fluorescence microscope 186. For excitation, we employed the 488 nm emission of an argon-ion laser with a maximum intensity at the sample surface of 1.00±0.05 mW. All images were collected with a 10×/0.3 Plan Neofluar air objective with a working distance of 5.6 mm. The image size was 128×128 with a pixel dwell time of 51.2 µs, corresponding to a total scanned area of ~900 µm$^2$. The pinhole size was 150 µm and the laser intensity was set at 10%. The detector gain, being a measure for the photomultiplier (Zeiss) voltage in arbitrary units, was set at 1000 for all measurements. For photo bleaching experiments, the laser intensity was set at 100% for 15 minutes. Bleaching an area of 20×800 µm.

The first series of measurements described in the following refers to the most stable, fully complementary duplexes. The areal density is approximately 10$^{12}$ duplexes per cm$^2$, meaning that the distance from one bound duplex to the next one is slightly less than the total length of an individual duplex. For optical reference purposes, unrelated to the heat-transfer measurement itself, the target DNA was labelled with fluorescent labels. This 'DNA-chip' was pressed mechanically with its backside onto a polished copper block, serving as heat provider or heat sink. The internal temperature of the copper block, $T_1$, was measured by a thermocouple and steered via a PID controller connected to a power resistor. Possible heat-transfer losses between copper and silicon were minimized by conductive silver paint. The front side of the DNA chip was exposed to 1×PBS buffer in a Perspex-made liquid cell: via an O-ring seal, a contact area was defined between the chip and the liquid. Except for minor heat losses along the seal, heat could only be transferred from the chip to the liquid because the chip did not touch the surrounding Perspex material. The temperature in the liquid, $T_2$, was measured by a second thermocouple, which was positioned at a distance of 1.7 mm from the solid-liquid interface. In order to validate that a heat transfer measurement can indeed give information on DNA-binding or denaturation, the cell also featured a gold electrode in the liquid, which was connected to the copper back contact via a home-made impedance analyser, allowing a cross-check via impedance measurements using a technique as described by van Grinsven in an international patent application entitled "A biosensor using impedimetric real-time monitoring" and co-pending herewith. Furthermore, a glass window allowed for optical monitoring with an inverted confocal fluorescence microscope, allowing a further cross-check.

Figure 3:
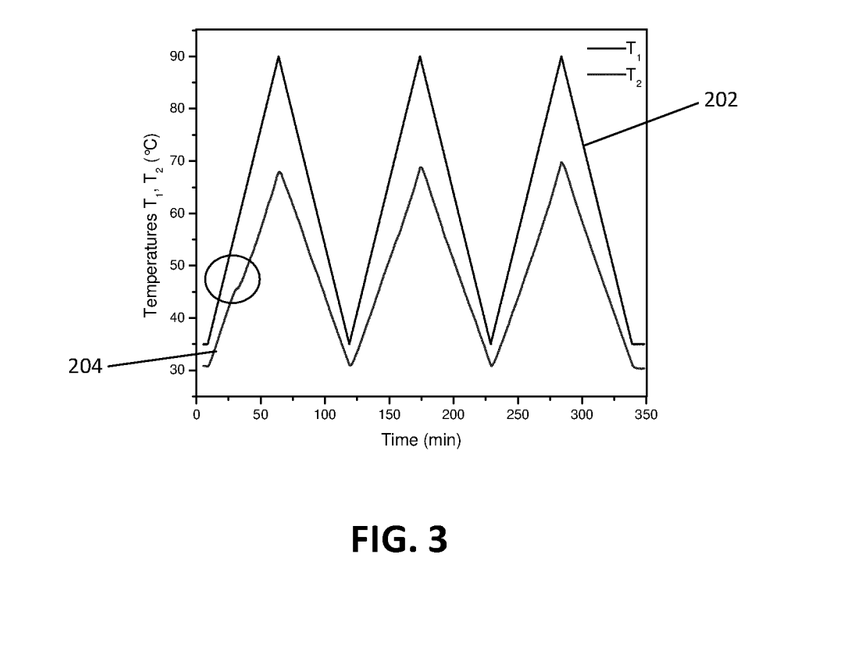
FIG. 3 illustrates the effect of three subsequent heating and cooling cycles on an electrode with immobilized probe DNA thereon, illustrating the effect as can be used in embodiments according to the present invention.
Figure 4:
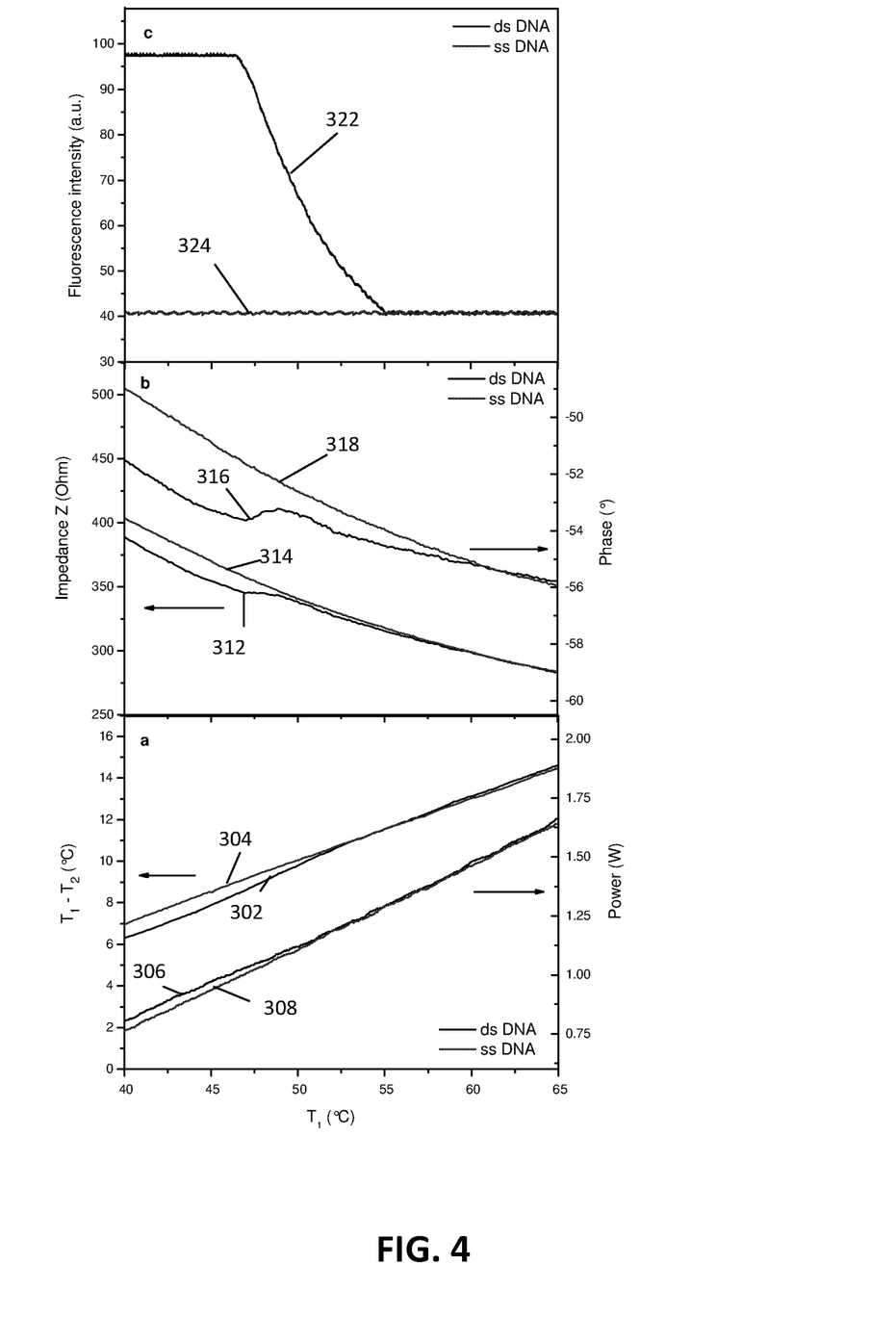
FIG. 4 illustrates a compilation of thermal data (a), impedimetric data (b) and fluorescence intensity (c) measured for a first heating run for a sample with double-stranded DNA and for a second heating run, illustrating the effect as can be used in embodiments according to the present invention.

During the measurement $T_1$ was increased with a heating rate of +1° C./min from 35 to 90° C. and cooled at the same rate back to 35° C. This was performed for three consecutive runs and the time dependence of $T_1$ and $T_2$ are shown in FIG. 3. Curve 202 illustrates the temperature $T_1$ of the Cu back contact, while curve 204 illustrates the liquid temperature $T_2$. Note that during the first heating, an anomalous behaviour of $T_2$ occurs, encircled, which was absent during the second and the third run and which is associated with the double-helix melting. As a starting condition, the probe DNA was hybridized with a complementary target. This first-run temperature anomaly was also found with three other diamond-coated Si electrodes, meaning that the effect is intrinsic. FIG. 4 presents a more refined analysis confirming this result.

FIG. 4 panel (a) shows the temperature difference $\Delta T=T_1-T_2$ as a function of $T_1$, with the curve 302 corresponding to the first heating run (supposed denaturation of ds-DNA) while the curve 304 presents the second heating with only ss-DNA on the chip. Both curves coincide at temperatures above the assumed melting temperature $T_m$~55° C. Panel (a) also includes the temperature dependence of the electrical heating power P, which was required to achieve the linear raise of $T_1$ according to the imposed heating rate. Curve 306 corresponds with the first heating run, while curve 308 corresponds with the second heating run. Also here we find a difference between the ds- and ss-DNA chip, which disappears above 55° C.

FIG. 4, panel (b) shows the $T_1$ dependence of the amplitude and the phase angle of the impedance signal at a frequency of 1 kHz with again a strong, anomalous feature during the first heating run. The temperature dependence of the amplitude of the impedance signal is shown in curve 312 for the first heating run and in curve 314 for the second heating run, while the temperature dependence of the phase angle of the impedance signal is shown in curve 316 for the first heating run and in curve 318 for the second heating run. Within previous studies under isothermal conditions (room temperature), it was observed that electrodes with ds-DNA have slightly higher impedance than their denatured ss-counterparts, an effect in the order of 2%. Although the present data seem to contradict this, the temperature-dependent resistivity of electrolytes (here PBS) comes into play as a second effect. When looking at a fixed temperature such as $T_1$=40° C., the temperature $T_2$ found in the liquid is about 1° C. higher with the ds-DNA electrode as compared to the ss-DNA state. In this temperature- and frequency range, the impedance drops by 2-3% for each additional ° C., explaining naturally the 'low' impedance of the ds-electrode for temperatures below $T_m$. Therefore, the temperature dependence of the impedance signal is a superposition of the denaturation at the solid-liquid interface (DNA molecular brush) and the heat transfer effect. The impedimetric signature as such is sharp with a pronounced local maximum of the phase angle.

The temperature dependence of the fluorescence-intensity signal is shown in the topmost FIG. 4 panel (c): during denaturation, the fluorescence intensity drops to its background value, which originates from reflected or strayed laser light. The denatured sample shows this background intensity at all temperatures. During increase of the temperature from 35° C. to 85° C. with 1° C. per minute, a confocal picture is taken every 1.4 seconds. When calculating and normalizing the fluorescence intensity, a bleached area as a reference. By using the ratio between the bleached are and non-bleached area as a measure for fluorescence intensity, the bias resulting from possible laser intensity fluctuations was removed. Fluorescence images were processed and the average fluorescence intensities were retrieved using the ImageJ1.44 software package. Curve 322 illustrates the fluorescence intensity for the first heating run, while curve 324 illustrates the fluorescence intensity for the second heating run. The fluorescence intensity is shown in arbitrary units. With increasing temperature a decrease in fluorescence intensity is seen starting at 46° C. which reaches its minimum at 55° C. At this temperature the fluorescence intensity is no longer distinguishable from the bleached area. Labelled target-DNA (in the present example being labelled using Alexa488), removed from the immobilized probe-DNA cannot contribute to the signal anymore because the confocal volume is limited to a maximum of 5 μm at the liquid side of the solid-liquid interface. This fluorescence test is a stringent and independent control because it is electronically and physically decoupled from the rest of the setup, which is steering and monitoring $T_1$ and $T_2$ and measuring the impedance values. Therefore, the fluorescence measurement can in no way be affected by (theoretical) electronic crosstalk between the temperature- and the impedance measurement circuits. Also, it is independent of interrelated physical effects like heat transfer and temperature-dependent impedance. The above results illustrate that the temperature anomaly relates one-to-one to the thermally induced denaturation of ds-DNA, which changes the heat transfer resistance at the solid-liquid interface, thus indicating the surprisingly effect that is used in embodiments according to the present invention.

Figure 5:
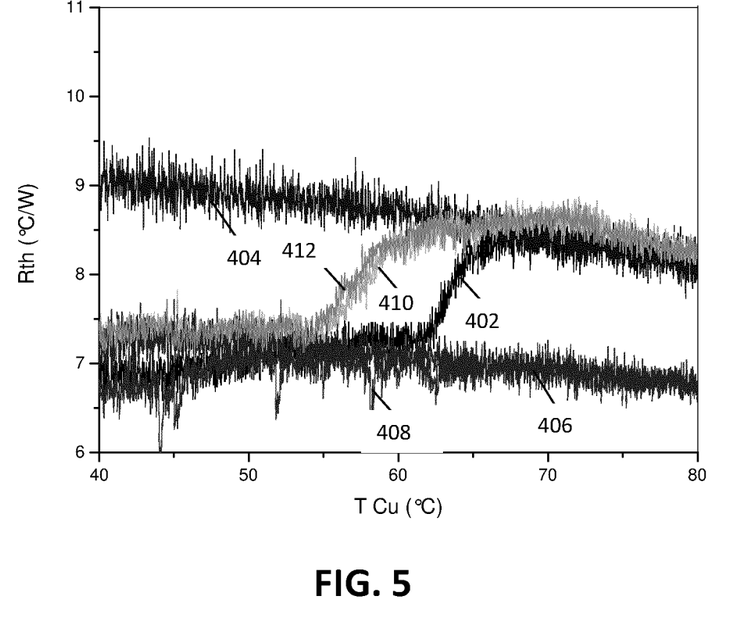
FIG. 5 illustrates the heat transfer resistance $R_{th}$ as function of temperature for initially single stranded DNA, for double stranded DNA and for defective DNA, illustrating effects as can be used in embodiments according to the present invention.

In order to extract the heat-transfer resistance $R_{th}$ at the solid-liquid interface quantitatively, for all temperatures $T_1$ the ratio of the temperature difference $\Delta T = T_1 - T_2$ and the input power P according to $R_{th} = \Delta T/P$ was analysed. $R_{th} = \Delta T/P$ is the standard definition of heat transfer resistance as known in the field and used in the description of the present invention. The resulting data for the heat transfer resistance are summarized in FIG. 5, indicating the obtained results for one sample. The data shown are non-filtered, raw data (resulting in noisy appearance): while the temperature $T_1$ is strictly linear and smooth in time, the required heating power shows small fluctuations within short time periods. Where required for ease of interpretation, the data can be smoothed. In case of the ds-DNA chip a low-temperature value of $R_{th} = 7.8°$ C./W is found, which starts to increase around 46° C. and reaches a new equilibrium value of 9.0° C./W at and above 55° C. (curve 402 corresponds with the double stranded DNA having a full match). The midpoint of the transition is found at $T_{midpoint} = 51.0°$ C.±0.5° C. This increase of the absolute $R_{th}$ value is a substantial effect, keeping in mind that the DNA brush is only a miniscule component (the fragment length corresponds to 10 nm) as compared to the total heat-transfer path with a geometrical distance of almost 3 mm between the two thermocouples. Performing the same $R_{th}$ analysis with the ss-DNA chip during the second heating run resulted in an almost temperature independent $R_{th}$ of 9.0° C./W (curve 404 corresponds with single stranded DNA). The $R_{th}$ for the same chip without any DNA, only with the fatty-acid linker layer, is also widely temperature independent with a value of 7.5° C.-7.8° C./W (curve 406 corresponds with a chip with fatty-acid). In this sense, the heat-transfer behaviour of the ds-DNA chip is comparable to a non-functionalized, naked chip (curve 408 corresponds with the chip having the diamond coating), while a brush of single-stranded DNA acts as an efficient insulator for heat transport. It is emphasized that this $R_{th}$ effect is fully reproducible for different sensor chips including the absolute values of $R_{th}$ for the different coating conditions (fatty-acid only, ds- and ss-DNA). These analyses have also been performed after hybridizing the probe DNA with the SNP-type fragments, generating defective duplexes with unmatched nucleotides at base-pair 7 (curve 410) and at base-pair 20 (curve 412). The overall behaviour of $R_{th}$ is similar to the complementary duplexes, but the midpoint temperatures are reduced for the base-pair 7 mismatch and the mismatch on base-pair 20. TABLE 2 gives a compilation of the midpoint temperatures $T_{midpoint}$ found by the heat-transfer approach for the three types of duplexes under study and calculated melting-temperature values that were obtained with three different processing techniques. The data are averages obtained based on three measurements. Despite of differences in absolute temperature values, the hierarchy of the stability is consistent, meaning that the complementary duplex has the highest melting- or midpoint temperature, followed by duplexes with the base-pair 7 defect and duplexes with the base-pair 20 defect are least stable. The data indeed correlate with the time-constants of isothermal, chemically induced denaturation using a method as described by van Grisven in the international patent application entitled "A biosensor using impedimetric real-time monitoring" and co-pending herewith. Finally, it was also studied whether the relatively low melting temperatures found here are related to the specific low-temperature hybridization at 30° C. Hybridizing the ss-DNA chip again under identical buffer- and time conditions with the complementary ss-DNA, but now at 50° C., gave an almost identical $R_{th}$ trace. It was also found that the hybridization temperature has only a minor influence on the absolute value of $T_{midpoint}$ and the mild hybridization at 30° C. already guarantees reliable data on the relative stability of complementary and defective duplexes.

TABLE 1

Sequences

```
Probe DNA
3'-CCA AGC CCC CAT ATG TAC CCG ACG TCC CCA AAA AAA C₆H₁₂-NH₂-5'
(SEQ ID NO: 1)

Full match
5'-Alexa 488-C₆H₁₂ GGT TCG GGG GTA TAC ATG GGC TGC AGG GG-3'
(SEQ ID NO: 2)

Mismatch at BP 7
5'-Alexa 488-C₆H₁₂ GGT TCG GGG GTA TAC ATG GGC TCC AGG GG-3'
(SEQ ID NO: 3)

Mismatch at BP 20
5 -Alexa 488-C₆H₁₂ GGT TCG GGG CTA TAC ATG GGC TGC AGG GG-3'
(SEQ ID NO: 4)

Random sequence
5'-Alexa 488-C₆H₁₂ TCA AAT TGC CAG AAC AAC TAC TGA CTG AA-3'
(SEQ ID NO: 5)
```

TABLE 2

| | $T_{midpoint}$ (°C.) This work | Denat. time constant $\tau$ | $T_{melting}$ (°C.) method 1 | $T_{melting}$ (°C.) method 2 | $T_{melting}$ (°C.) Method 3 |
|---|---|---|---|---|---|
| Complement | 55.5 | 2.26 min | 81.7 | 72.9 | 81.6 |
| Mismatch BP 7 | 47.5 | 1.16 min | 77.7 | 69.1 | 77.1 |
| Mismatch BP 20 | 47.8 | 1.38 min | 76.2 | 67.8 | 75.1 |

The invention claimed is:

1. A bio-sensing device suitable for the detection and/or characterization of target DNA and/or RNA bioparticles, the bio-sensing device comprising
a heating element configured to heat using a power, the heating element being suitable for providing thermal denaturation of target DNA and/or RNA bioparticles,
a sample holder adapted for receiving a biocompatible substrate having a functionalized surface that is coated with probe DNA and/or RNA to which target DNA and/or RNA duplexes can be attached, the sample holder further being adapted for exposing the biocompatible substrate at one side to the heating element,
a first temperature sensor configured to sense a temperature at the side where the biocompatible substrate can be exposed to the heating element and a second temperature sensor configured to sense a temperature at the side opposite thereto with respect to the biocompatible substrate, and
a processing means programmed for calculating at least one heat transfer resistivity value based on temperature values obtained with the first temperature sensor and the second temperature sensor and the power for the heating element, the heat transfer resistivity value being defined as $\Delta T/P$, in which P is the power of the heating element and $\Delta T$ is the difference between the temperature value of the first temperature sensor and the temperature value of the second temperature sensor, for deriving a characteristic of the target DNA and/or RNA bioparticles from said heat transfer resistivity value.

2. A biosensing device according to claim 1, wherein the processing means is adapted for determining a heat transfer resistivity as function of temperature.

3. A biosensing device according to claim 2, wherein the processing means is adapted for determining at least two heat transfer resistivity values as function of temperature, one at a temperature sensed with the first temperature sensor below the expected thermal denaturation temperature as sensed with the first temperature sensing element and one at a temperature above the expected thermal denaturation temperature as sensed with the first temperature sensor.

4. A biosensing device according to claim 1, wherein the biosensing device comprises a fluidic compartment configured to expose the side of the biocompatible substrate opposite the heating element to a fluid, the second temperature sensor being positioned in the fluid compartment.

5. A biosensing device according to claim 1, wherein the processing means is adapted for determining a characteristic of the target DNA and/or RNA duplexes based on the at least one heat transfer resistivity.

6. A biosensing device according to claim 5, wherein the characteristic of the target DNA and/or RNA duplexes is at least one point mutation therein.

7. A biosensing device according to claim 1, wherein the heating element is configured to be controlled by a power resistor configured to provide an input power to the heating element.

8. A biosensing device according to claim 1, wherein the first temperature sensor and/or the second temperature sensor is a thermocouple.

9. A biosensing device according to claim 1, the biosensing device comprising a controller configured to control the heating element and to control the temperature sensors for obtaining input power and temperature values for different temperatures as sensed with the first temperature sensor.

10. A method for characterizing a target DNA and/or RNA bioparticle, the method comprising
providing a bio-sensing device according to claim 1;
obtaining a biocompatible substrate comprising a first side having a functionalized surface which is coated with probe DNA and/or RNA whereto the target DNA and/or RNA bioparticles are attached,
disposing the biocompatible substrate in the sample holder such that the first side can be exposed to the heating element;
providing a heating power to the first side of the biocompatible substrate using the heating element,
sensing at least a temperature at the first side of the biocompatible substrate using the first temperature sensor and at a second side, opposite to the first side with respect to the biocompatible substrate, using the second temperature sensor and
calculating at least one heat transfer resistivity value based on the temperature values obtained at the first side and the second side and the power using the processing means; and deriving a characteristic of the target DNA and/or RNA from said heat transfer resistivity value.

11. A method according to claim 10, wherein said calculating comprises determining a heat transfer resistivity as function of temperature.

12. A method according to claim 11, wherein determining a heat transfer resistivity as function of temperature comprises determining at least two heat transfer resistivity values as function of temperature, one at a temperature sensed with the first temperature sensor below the expected thermal denaturation temperature as sensed with the first temperature sensor and one at a temperature above the expected thermal denaturation temperature as sensed with the first temperature sensor.

13. A method according to claim 10, wherein the method comprises providing a fluid in contact with the functionalized surface which is coated with probe DNA and/or RNA.

14. A method according to claim 10, wherein said obtaining biocompatible substrate comprises attaching the target DNA and/or RNA bioparticles to a functionalized surface which is coated with probe DNA.

15. A method according to claim 10, wherein said substrate is nanocrystalline diamond.

16. A method according to claim 10, wherein the substrate is a semiconductor substrate having a diamond coating with a thickness between 50 nm and 150 nm on at least one of its surface.

17. A method according to claim 10, wherein the functionalized surface comprises a first layer of fatty acid(s).

18. A method according to claim 10, wherein the functionalized surface comprises a second layer provided onto said first layer and containing the probe DNA and/or RNA.

19. A method according to claim 10, wherein the probe DNA and/or RNA bioparticles is NH2-modified single stranded DNA (ssDNA).

20. A method according to claim 19, wherein attaching the target DNA and/or RNA bioparticles to the functionalized surface is performed by hybridization of target DNA duplexes with the probe ssDNA molecules.

* * * * *

SEQUENCE LISTING

<160> NUMBER OF SEQ ID NOS: 5

<210> SEQ ID NO 1
<211> LENGTH: 36
<212> TYPE: DNA
<213> ORGANISM: Artificial Sequence
<220> FEATURE:
<223> OTHER INFORMATION: Synthetic; Probe DNA
<220> FEATURE:
<221> NAME/KEY: modified_base
<222> LOCATION: (1)..(1)
<223> OTHER INFORMATION: 6-aminohexyl modification at 5'

<400> SEQUENCE: 1
aaaaaaaccc ctgcagccca tgtataccccc cgaacc                          36

<210> SEQ ID NO 2
<211> LENGTH: 29
<212> TYPE: DNA
<213> ORGANISM: Artificial Sequence
<220> FEATURE:
<223> OTHER INFORMATION: Synthetic; full match
<220> FEATURE:
<221> NAME/KEY: modified_base
<222> LOCATION: (1)..(1)
<223> OTHER INFORMATION: 6-(Alexa 488 dye)-hexyl modification at 5'

<400> SEQUENCE: 2
ggttcggggg tatacatggg ctgcagggg                                   29

<210> SEQ ID NO 3
<211> LENGTH: 29
<212> TYPE: DNA
<213> ORGANISM: Artificial Sequence
<220> FEATURE:
<223> OTHER INFORMATION: Synthetic; Mismatch at BP7
<220> FEATURE:
<221> NAME/KEY: modified_base
<222> LOCATION: (1)..(1)
<223> OTHER INFORMATION: 6-(Alexa 488 dye)-hexyl modification at 5'

<400> SEQUENCE: 3
ggttcggggg tatacatggg ctccagggg                                   29

<210> SEQ ID NO 4
<211> LENGTH: 29
<212> TYPE: DNA
<213> ORGANISM: Artificial Sequence
<220> FEATURE:
<223> OTHER INFORMATION: Synthetic; Mismatch at BP 20
<220> FEATURE:
<221> NAME/KEY: modified_base
<222> LOCATION: (1)..(1)
<223> OTHER INFORMATION: 6-(Alexa 488 dye)-hexyl modification at 5'

<400> SEQUENCE: 4
ggttcggggc tatacatggg ctgcagggg                                   29

```
<210> SEQ ID NO 5
<211> LENGTH: 29
<212> TYPE: DNA
<213> ORGANISM: Artificial Sequence
<220> FEATURE:
<223> OTHER INFORMATION: Synthetic; random sequence
<220> FEATURE:
<221> NAME/KEY: modified_base
<222> LOCATION: (1)..(1)
<223> OTHER INFORMATION: 6-(Alexa 488 dye)-hexyl modification at 5'

<400> SEQUENCE: 5
tcaaattgcc agaacaacta ctgactgaa                                          29
```